United States Patent [19]

Harada et al.

[11] Patent Number: 4,576,915

[45] Date of Patent: Mar. 18, 1986

[54] STRAINS OF *RHIZOBIUM PHASEOLI* AND PREPARATION OF CYCLIC (1→2)-β-D-GLUCAN

[75] Inventors: Tokuya Harada; Tadashi Higashiura; Misae Okubo, all of Osaka, Japan

[73] Assignee: Daikin Kogyo Co., Ltd., Osaka, Japan

[21] Appl. No.: 542,217

[22] Filed: Oct. 14, 1983

[30] Foreign Application Priority Data

Oct. 14, 1982 [JP] Japan .................................. 57-180949

[51] Int. Cl.$^4$ .......................... C12P 19/04; C12R 1/41
[52] U.S. Cl. ................................. 435/101; 435/246; 435/812; 435/878; 435/253
[58] Field of Search ................ 435/101, 246, 812, 878

[56] References Cited

U.S. PATENT DOCUMENTS

| | | | |
|---|---|---|---|
| 3,616,236 | 10/1971 | Delin | 435/878 |
| 4,094,097 | 6/1978 | Alexander et al. | 435/878 |
| 4,400,466 | 8/1983 | Azoulay | 435/878 |

OTHER PUBLICATIONS

Chemical Abstracts, vol. 96, No. 11, Mar. 15, 1982, p. 318, Abstract No. 82465.
Chemical Abstracts, vol. 97, No. 3, Jul. 19, 1982, p. 404, Abstract No. 20352.
XI$^{th}$ International Carbohydrate Symposium, Aug. 22-28, 1982.
Zevenhuizen, "Antonie van Leeuwenhoek", 47 (1981) 481-497.
Bergey's Manual of Determinative Bacteriology, Eighth Edition, pp. 261-265.

*Primary Examiner*—Sam Rosen
*Assistant Examiner*—William J. Herald
*Attorney, Agent, or Firm*—Birch, Stewart, Kolasch & Birch

[57] ABSTRACT

Novel strains of *Rhizobium phaseoli* which do not produce acidic extracellular polysaccharides or their constituents, which produces cyclic β-1,2-glucan effectively.

13 Claims, No Drawings

STRAINS OF *RHIZOBIUM PHASEOLI* AND PREPARATION OF CYCLIC (1→2)-β-D-GLUCAN

The present invention relates to novel strains belonging to genus Rhizobium and the preparation of cyclic (1→2)-β-D-glucan (hereinafter referred to as cyclic β-1,2-glucan) by the use of said novel strain. More particularly, it relates to novel variant strains of genus Rhizobium and a process for preparing cyclic β-1,2-glucan by the use of said novel variant strains.

It is known that cyclic β-1,2-glucan can improve the growth of root nodule of plants (cf. Plant and Soil, 64 (3), 315–324). Cyclic β-1,2-glucan may be used, like cyclodextrin, to produce clathrate compounds.

It is also known that strains belonging to genus Rhizobium produce cyclic β-1,2-glucan (cf. Antonie van Leeuwenhoek, 45, 165–175 (1979) and 47, 481–497 (1981), and Nippon Nogeikagakukai Taikai Yoshishu, 570 (1982)).

However, the known strains belonging to genus Rhizobium show low productivity of cyclic β-1,2-glucan and produce simultaneously acidic extracellular polysaccharides, which increase viscosity of a culture medium and make the cultivation of the strain difficult due to foaming under aeration.

As a result of the extensive study of the production of cyclic β-1,2-glucan by the use of strains belonging to genus Rhizobium, it has now been found that certain specific variant strains belonging to genus Rhizobium have high productivity of cyclic β-1,2-glucan and do not produce the acidic extracellular polysaccharides or their constituents.

According to the present invention, there is provided a novel strain belonging to genus Rhizobium which does not produce acidic extracellular polysaccharides or their constituents.

Typical strains of the invention are *Rhizobium phaseoli* RA-4 (FERM BP-374), *Rhizobium phaseoli* RA-8 (FERM BP-379) and *Rhizobium phaseoli* RA-12 (FERM BP-380). All of them were obtained by mutating a known strain, *Rhizobium phaseoli* AHU-1133, and were deposited at Fermentation Research Institute, Agency of Industrial Science and Technology in Japan under the Budapest Treaty under the deposition numbers as described above.

The mycological characteristics of these strains are the same as those of *Rhizobium phaseoli* AHU-1133 except that the strains of the invention do not produce the acidic extracellular polysaccharides.

The mutation of the strain can be carried out by per se conventional methods, for example, by irradiation of UV light or high energy radiation or by the treatment with chemicals (eg. N-methyl-N'-nitro-N'-nitrosoguanidine). The mutated strains are cultivated on an agar plate culture medium, and from grown colonies, comparatively small ones having non-glossy surfaces are selected, thereby strains which do not produce the acidic extracellular polysaccharides are obtained.

According to the invention, cyclic β-1,2-glucan is prepared by cultivating the strain of the invention in a culture medium to produce cyclic β-1,2-glucan in the culture medium and recovering produced cyclic β-1,2-glucan from the culture medium.

The culture medium contains carbon sources which can be utilized by the strains (eg. glucose, mannitol, sucrose, molasses, etc.), nitrogen sources which can be metabolized by the strains (eg. yeast extract, peptone, corn steep liquor, ammonia, ammonium sulfate, ammonium nitrate, etc.) and various inorganic salts which are essential to the growth of the strains.

The strain is usually cultivated under an aerobic condition, for example, by shaking culture or submerged culture under aeration at a temperature of from 20° to 40° C., preferably from 25° to 35° C., particularly at about 30° C. During the cultivation, pH of the culture medium is adjusted with a suitable acid or base such as sulfuric acid or sodium hydroxide to 5 to 8, preferably 6.5 to 7.5, particularly about 7.2. The cultivation time is at least 24 hours. Preferably, in the case of the shaking culture, it is from 3 to 10 days and in the case of the submerged culture under aeration by means of, for example, a jar fermenter, it is from 3 to 7 days. Under these cultivation conditions, cyclic β-1,2-glucan is produced in a high yield.

After the cultivation of the strain, the strain cells are removed from the culture medium by a per se conventional method such as centrifugation, and the medium is concentrated. Then, an organic liquid such as ethanol is added in the medium and again centrifuged to remove the residual strain cells and polysaccharides contained in the medium. By the addition of the organic liquid in the supernatant liquid, crude cyclic β-1,2-glucan is precipitated. The crude cyclic β-1,2-glucan can be purified by a per se conventional method, for example, gel filtration.

As described above, since the novel variant strains belonging to genus Rhizobium of the invention do not produce any acidic extracellular polysaccharide, the viscosity of the culture medium does not increase, and the culture medium is hardly foamed under aeration. Therefore, the strains of the invention is effectively cultivated.

The present invention will be hereinafter explained further in detail by the following Examples.

EXAMPLE 1

*Rhizobium phaseoli* AHU-1133 was cultivated in the YPG culture medium containing yeast extract (1 g/dl), polypeptone (1 g/dl) and glucose (2 g/dl) at 30° C. for 24 to 48 hours and then suspended in 0.05 M tris-maleate buffer solution (pH 6.0) containing N-methyl-N'-nitro-N'-nitrosoguanidine (200 μg/ml) in a concentration of $10^5$ to $10^7$ cells/ml. The suspension was shaken at 30° C. for 30 minutes and centrifuged at 10,000 rpm for 5 minutes to recover the strain cells, which were suspended in physiological saline solution. The strain cells were washed with physiological saline solution twice and suspended in physiological saline solution in a concentration of about $10^3$ to $10^4$ cells/ml.

The thus prepared suspension (0.1 ml) was coated on an agar plate culture (glucose, 2 g/dl; NH4Cl, 0.2 g/dl; KH2PO4, 0.21 g/dl; Na2HPO4.12H2O, 1.2 g/dl; MgSO4.7H2O, 0.03 g/dl; Na2SO4, 0.05 g/dl; yeast extract, 0.1 g/dl and agar, 2 g/dl) and cultivated at 30° C. for 3 to 4 days. From the grown colonies, a comparatively small one having non-glossy surface was selected to obtain a strain which does not produce any acidic extracellular polysaccharide, which is named *Rhizobium phaseoli* RA-4 (FERM BP-374).

EXAMPLES 2 AND 3

In the same manner as in Example 1, *Rhizobium phaseoli* RA-8 (FERM BP-379) and *Rhizobium phaseoli* RA-12 (FERM BP-380) were obtained.

EXAMPLE 4

In distilled water (1 l), glucose (40 g), $(NH_4)_2$-$HPO_4$ (1.5 g), $KH_2PO_4$ (1.0 g), $MgSO_4.7H_2O$ (0.5 g), NaCl (10 mg), $CaCl_2$ (10 mg), $MnCl_2.4H_2O$ (10 mg), $CuSO_4.5H_2O$ (50 μg), $Na_2MoO_4.2H_2O$ (20 μg), $H_3BO_4$ (10 μg), biotin (200 μg), thiamine (20 μg) and $CaCO_3$ (5 g) were added to prepare a culture medium. The culture medium (100 ml) was adjusted to pH of 7.2 with 1N sulfuric acid or 1N sodium hydroxide and then charged in 500 ml Erlenmeyer flask and sterilized.

*Rhizobium phaseoli* RA-4 which had been prefermented in the culture medium as prepared above was inoculated in the same culture medium and cultivated at 30° C. with rotation at 220 rpm.

After being cultivated for 6 days, acetone (150 ml) was added in the medium and centrifuged at 5,000 rpm for 5 minutes. The supernatant was concentrated to 30 ml. In the concentrated supernatant, ethanol (60 ml) was added and again centrifuged at 10,000 rpm for 5 minutes to precipitate the residual strain cells and polysaccharides. Form the supernatant, powdery or fibrous white crude cyclic β-1,2-glucan was precipitated by the addition of ethanol (360 ml), which crude product was collected by centrifugation at 10,000 rpm for 15 minutes. The collected product was washed with ethanol twice and dried under reduced pressure at 40° C. to obtain crude cyclic β-1,2-glucan.

The crude product was developed on Sephadex (trade mark) G-25 column (diameter, 26 mm; length, 500 mm) with pure water to obtain a fraction (110 ml) containing cyclic β-1,2-glucan. The fraction was concentrated to 10 ml. In the concentrate, ethanol (100 ml) was added to precipitate powdery white cyclic β-1,2-glucan, which was recovered by centrifugation at 10,000 rpm for 15 minutes. The product was washed with ethanol twice and dried under reduced pressure at 40° C. to obtain pure cyclic β-1,2-glucan (54.9 mg).

$^{13}$C-NMR: δ=102.7, 82.6, 77.1, 76.2, 69.7 and 61.5 ppm (internal standard; dioxane).

In the course of the cultivation, the viscosity of the medium did not increase even at the final stage of cultivation and the medium was flowable and foamed slightly.

A part of the thus obtained product was hydrolyzed by a per se conventional method. A part of the hydrolized product was analyzed by paper chromatography, and the other part was alditol-acetated and analyzed by gas chromatography. In both cases, only glucose was found. The angle of rotaion of the obtained product was −5°. Further, the obtained product was methylated, hydrolyzed and alditol-acetated, and then analyzed by GC-MS, and it was found from the results that 1- and 2-positions of glucose participated in the bonding of cyclic β-1,2-glucan.

EXAMPLE 5

In the same manner as in Example 4 but using *Rhizobium phaseoli* RA-8 in place of *Rhizobium phaseoli* RA-4, cyclic β-1,2-glucan (70.2 mg) was obtained.

EXAMPLE 6

In the same manner as in Example 4 but using *Rhizobium phaseoli* RA-12 in place of *Rhizobium phaseoli* RA-4, cyclic β-1,2-glucan (59.2 mg) was obtained.

COMPARATIVE EXAMPLE 1

In the same manner as in Example 4 but using *Rhizobium phaseoli* AHU-1133 in place of *Rhizobium phaseoli* RA-4, cyclic β-1,2-glucan (9.83 mg) was obtained.

In this cultivation, the viscosity of the medium increased at the final stage and the flowability of the whole medium deteriorated.

What is claimed is:

1. A novel strain of *Rhizobium phaseoli* which produces cyclic β-1,2-glucon, but does not produce acidic extracellular polysaccharides or constituents of said acidic extracellular polysaccharides.

2. A novel strain according to claim 1, which is obtained by mutating *Rhizobium phaseoli* AHU-1133.

3. A novel strain according to claim 2, which is *Rhizobium phaseoli* RA-4 (FERM BP-374).

4. A novel strain according to claim 2, which is *Rhizobium phaseoli* RA-8 (FERM BP-379).

5. A novel strain according to claim 2, which is *Rhizobium phaseoli* RA-12 (FERM BP-380).

6. A process for preparing cyclic β-1,2-glucan, which comprises cultivating a novel strain of *Rhizobium phaseoli* which does not produce acidic extracellular polysaccharides or constituents of said acidic extracellular polysaccharides, in a culture medium to produce cyclic β-1,2-glucan and recovering said cyclic β-1,2-glucan from said culture medium.

7. A process according to claim 6, wherein the strain is *Rhizobium phaseoli* RA-4 (FERM BP-374).

8. A process according to claim 6, wherein the strain is *Rhizobium phaseoli* RA-8 (FERM BP-379).

9. A process according to claim 6, wherein the strain is *Rhizobium phaseoli* RA-12 (FERM BP-380).

10. A process according to claim 6, wherein the cultivation temperature is from 20° to 40° C.

11. A process according to claim 6, wherein the pH of the culture medium is from 5 to 8.

12. A process according to claim 6, wherein the cultivation time is at least 24 hour.

13. A process according to claim 6, and further comprising the step of purifying the crude cyclic β-1,2-glucan.

* * * * *